(12) United States Patent
Cho et al.

(10) Patent No.: US 7,488,291 B2
(45) Date of Patent: Feb. 10, 2009

(54) METHODS FOR DETECTING AND MONITORING SLEEP DISORDERED BREATHING USING AN IMPLANTABLE MEDICAL DEVICE

(75) Inventors: Yong K. Cho, Maple Grove, MN (US); Tommy D. Bennett, Shoreview, MN (US); Barbro M. Kjellstrom, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 489 days.

(21) Appl. No.: 11/237,354

(22) Filed: Sep. 28, 2005

(65) Prior Publication Data

US 2007/0073171 A1    Mar. 29, 2007

(51) Int. Cl.
*A61B 5/02* (2006.01)
(52) U.S. Cl. ..................................... 600/486
(58) Field of Classification Search ................. 600/486
See application file for complete search history.

(56) References Cited

U.S. PATENT DOCUMENTS

| | | | |
|---|---|---|---|
| 4,428,378 A | 1/1984 | Anderson et al. | |
| 4,869,251 A | 9/1989 | Lekholm et al. | |
| 4,896,068 A | 1/1990 | Nilsson | |
| 5,052,388 A | 10/1991 | Sivula et al. | |
| 5,193,535 A | 3/1993 | Bardy et al. | |
| 5,233,984 A | 8/1993 | Thompson | |
| 5,314,430 A | 5/1994 | Bardy | |
| 5,330,505 A | 7/1994 | Cohen | |
| 5,353,752 A | 10/1994 | Suzuki | |
| 5,353,800 A | 10/1994 | Pohndorf et al. | |
| 5,368,040 A | 11/1994 | Carney | |
| 5,564,434 A | 10/1996 | Halperin et al. | |
| 5,630,834 A | 5/1997 | Bardy | |
| 5,814,087 A | 9/1998 | Renirie | |
| 6,024,704 A | 2/2000 | Meador et al. | |
| 6,152,885 A | 11/2000 | Taepke | |
| 6,398,728 B1 | 6/2002 | Bardy | |
| 6,865,419 B2 * | 3/2005 | Mulligan et al. | 607/23 |
| 7,207,945 B2 * | 4/2007 | Bardy | 600/529 |
| 2002/0103442 A1 | 8/2002 | Mulligan et al. | |
| 2004/0039263 A1 | 2/2004 | Bardy | |
| 2005/0043772 A1 * | 2/2005 | Stahmann et al. | 607/42 |

* cited by examiner

*Primary Examiner*—Charles A Marmor, II
*Assistant Examiner*—Christian Y Jang
(74) *Attorney, Agent, or Firm*—Reed A. Duthler

(57) ABSTRACT

A method of identifying sleep disordered breathing (SDB) in a patient includes monitoring a hemodynamic pressure, deriving high, middle, and low values representative of the distribution of the hemodynamic pressure over a storage interval, measuring a ratio of a lower range to a full range of the hemodynamic pressure based on the derived high, middle, and low values, and using the ratio to determine whether the patient has experienced an SDB episode. Certain embodiments of the invention compare the ratio to a threshold value to identify the occurrence of an SDB episode, while other embodiments of the invention identify the occurrence of an SDB episode by monitoring for a simultaneous increase in both the ratio and the full range of the hemodynamic pressure. In certain other embodiments of the invention, activity level and/or duration criteria may be employed to confirm the occurrence of an SDB episode detected using the ratio.

15 Claims, 10 Drawing Sheets

METHODS FOR DETECTING AND MONITORING SLEEP DISORDERED BREATHING USING AN IMPLANTABLE MEDICAL DEVICE

FIELD

The disclosure relates generally to the fields of heart failure management and sleep disordered breathing (SDB), and more particularly, to a method for screening heart failure patients for the presence of SDB.

BACKGROUND

Typically, patients with heart failure have a reduced capacity for myocardial function. The heart is unable to adequately meet the metabolic demands of the body by providing the appropriate blood flow. This may result in increased blood pressure (afterload), and increased volume retention (preload). Thus, common symptoms of ventricular dysfunction or heart failure include fatigue, which is caused by the low cardiac output, and edema and swelling, which is caused by fluid overload.

Current guidelines for the evaluation and management of chronic heart failure (HF) tend to focus on the presentation of subjects while they are awake. However, several recent studies have shown that sleep disordered breathing (SDB), commonly known as sleep apnea, may play an important role in the pathogenesis and progression of heart failure.

The prevalence of undiagnosed sleep apnea in the U.S. is thought to be in the millions with on the order of 2% of middle-aged women and 4% of middle-aged men having sleep apnea syndrome. See Young T. et al., "The occurrence of sleep-disordered breathing among middle-aged adults," *New England J. Med.* 1993;328:1230-1235. Sleep apnea is a condition that results from a reduction in air intake through the air passage of sleeping individuals. This problem arises as a result of weak muscle tone in the throat and, although compensated for during waking hours, gives rise to symptoms of fatigue during the day, poor quality sleep at night, and heavy snoring during sleep. Diagnosis of sleep apnea has been carried out in sleep laboratories where the patient is monitored at night during sleep in a process called nocturnal polysomnography. This diagnostic test is expensive, time consuming, and must be administered by highly trained technicians. Consequently, availability of the test is limited.

Sleep disordered breathing (SDB) is estimated to occur in about 60% of patients suffering from congestive heart failure (CHF; Rechtschaffen A, Kales A, eds. *A Manual of Standardized Technology, Techniques and Scoring System for Sleep Stages of Human Subjects.* Los Angeles: UCLA Brain Information Service/Brain Research Institute, 1968). Nasal continuous positive airway pressure (CPAP) has been advocated as a nonpharmacological treatment for patients with congestive heart failure and certain forms of SDB.

The clinical implications of SDB are not widely recognized and are seldom taken into account in the evaluation and management of heart failure (HF). The conventional approach to the evaluation and management of HF may need to be modified in view of a growing body of evidence showing that the acute and chronic mechanical, hemodynamic, autonomic, and chemical effects of SDB place subjects with HF at increased risk of accelerated disease progression. A convenient method of screening heart failure patients for the presence of SDB is therefore desired.

SUMMARY OF THE INVENTION

In certain embodiments of the invention, a method of identifying sleep disordered breathing (SDB) in a patient includes measuring a hemodynamic pressure parameter, periodically deriving statistical information about the hemodynamic pressure parameter at storage intervals, including values representative of the distribution of the hemodynamic pressure parameter over each storage interval, measuring a ratio of a lower range to a full range of the hemodynamic pressure parameter, and using the ratio to determine whether the patient has experienced an SDB episode. Further embodiments of the invention include comparing the ratio to a ratio threshold, or monitoring for an increase in both the ratio and the full range of the hemodynamic pressure parameter to identify an SDB episode.

In other embodiments of the invention, a method of identifying sleep disordered breathing (SDB) in a patient includes measuring a hemodynamic pressure parameter over a period of time, monitoring an activity level signal of a patient over the period of time, measuring a phase difference between the hemodynamic pressure parameter and activity level signals, and identifying the presence of SDB if the phase difference is greater than a threshold amount.

In certain other embodiments of the invention, a method of identifying sleep disordered breathing (SDB) in a patient includes measuring a hemodynamic pressure parameter signal over a period of time, monitoring an activity level signal of a patient over the period of time, classifying the activity level as being low when below a predetermined activity level, and, during a period of low activity level, identifying the presence of SDB when a change in the hemodynamic pressure parameter signal is greater than a specified amount.

DETAILED DESCRIPTION

Figure 1:
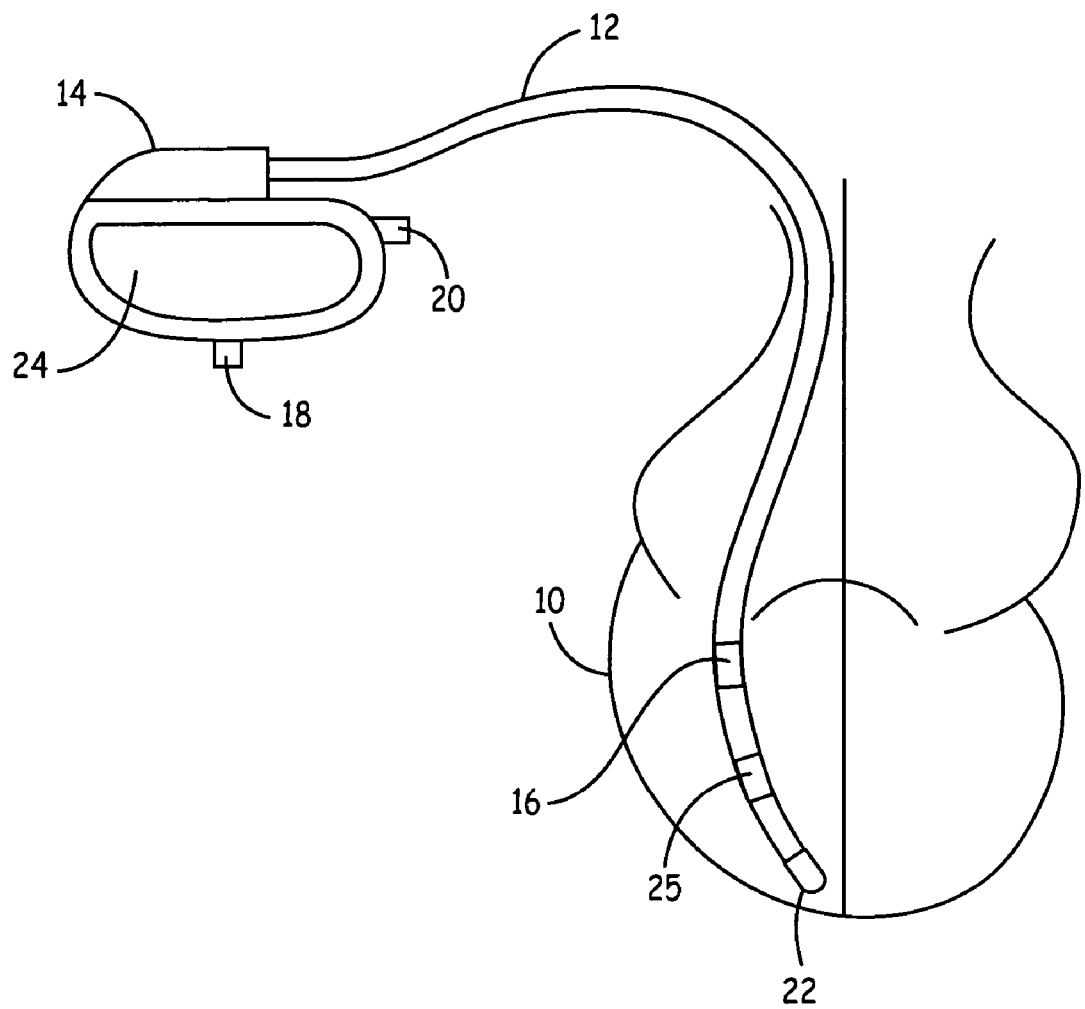
FIG. 1 is a schematic view of an implantable medical device (IMD) that may be used in accordance with certain embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

FIG. 1 is a schematic representation of an implantable medical device (IMD) 14 that may be used in accordance with certain embodiments of the invention. The IMD 14 may be any device that is capable of measuring pressure signals from within a ventricle of a patient's heart, and which may further be capable of measuring other signals, such as the patient's electrogram (EGM). Such a device may be an implantable hemodynamic monitor (IHM) such as the Chronicle™ device from the Medtronic Corporation. The Chronicle™ and its associated leads and circuitry are described in commonly-assigned U.S. Pat. Nos. 5,535,752; 5,564,434; 6,024,704; and 6,152,885, which are incorporated herein by reference in their entireties. Other pacing systems known in the art may be adapted for use in the alternative. The IMD may additionally, or in the alternative, include cardioversion/defibrillation circuitry as described in commonly-assigned U.S. Pat. Nos. 5,193,535, and 5,314,430, which are incorporated herein by reference in their entireties. Other devices such as implantable drug delivery devices may also be adapted for use with the current invention.

The leads and circuitry disclosed in the above-incorporated, commonly assigned, '752 and '434 patents can be employed to record EGM and absolute blood pressure values over certain time intervals. The recorded data may be periodically telemetered out to a programmer operated by a physician or other healthcare worker in an uplink telemetry transmission during a telemetry session.

With continued reference to FIG. 1, the IMD/IHM 14 may be implanted subcutaneously, between the skin and the ribs. Other implantation sites may be used if appropriate. In one embodiment, a lead 12 is passed through a vein into the right ventricle of the heart 10. The distal end of the lead or catheter may have a tip electrode 22 contacting the interior of the heart. In a multipolar configuration, a second ring electrode 25 may be spaced from the tip electrode 22. Each of these electrodes is connected to the circuitry contained in the IMD 14. Alternatively, a unipolar mode may be used wherein a portion of the metallic enclosure or "can" of the IMD may form an electrode surface 24. The EGM signal is measured between this surface and an implanted electrode such as the tip electrode 22. In yet another embodiment, a Subcutaneous Electrode Array (SEA) such as electrodes 18 and 20 may be located on, but electrically isolated from, the housing of the implantable device such as disclosed in U.S. Pat. No. 5,331,966, incorporated herein by reference in its entirety.

Lead 12 is shown to further include a pressure sensor 16. If desired, an additional lead coupled to IMD 14 may be provided to carry the pressure sensor. The pressure sensor is preferably located within the right ventricle, although it may also be located within the left ventricle. Pressure sensors and accompanying circuitry that may be adapted for use with embodiments of the invention are described in commonly-assigned U.S. Pat. Nos. 5,353,752, 5,353,800, 5,564,434, 5,330,505, and 5,368,040 which are incorporated herein by reference in their entireties.

A typical sleep apnea, or SDB, event is manifested by reduced airflow lasting approximately 10-30 seconds, followed by hyperventilation for approximately 10-20 seconds. In patients with moderate to severe SDB, SDB events tend to occur in clusters. The apnea-recovery cycles typically continue many times, and often last more than about 5 minutes. However, the cycles may continue for over an hour, causing oscillations in physiological parameters such as heart rate, hemodynamic pressures, and saturated oxygen ($SaO_2$) levels.

The existence of prolonged periods of apnea-recovery cycles may modify various hemodynamic parameters, such as RV pressures, to such an extent that the changes in hemodynamic parameters may serve as an indication of an SDB condition.

An implantable hemodynamic monitor (IHM), such as the Medtronic® Chronicle™, may be used for recording a variety of hemodynamic parameters in a HF patient, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording. Hemodynamic pressure parameters may be obtained by using a pressure sensor mounted on a lead to measure intracardiac blood pressures, including absolute and/or relative pressures. U.S. Pat. No. 6,865,419 to Mulligan et al., incorporated herein by reference in its entirety, discloses a method of deriving mean pulmonary arterial pressure (MPAP) from an IHM such as the Chronicle™.

Information collected by an IHM device such as the Chronicle™ can be retrieved and transmitted to an external device, or to a patient management network, or to a database, using various transmission methods including the Internet. For example, a patient may be able to activate the device to retrieve and transmit the data stored in the IHM to a remote system where additional processing may be performed on the data. This retrieval and transmission of stored data may be done on a periodic basis, such as once per week, to provide a convenient method of "continuous" monitoring of a patient. Stored data retrieved from the IHM and transmitted to a remote system may be available for transfer to a clinical center for review by a clinician. Data is preferably transferable to an internet-compatible central patient management network for remote monitoring. A bi-directional communication system that is network, Internet, intranet and worldwide web compatible to enable chronic monitoring based on data obtained from implantable monitors is generally disclosed in International Publication No. WO 01/70103 A2, to Webb et al, incorporated herein by reference in its entirety.

The data stored by an IHM may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a $94^{th}$ percentile value (i.e., the upper percentile), and a $6^{th}$ percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

During sleep apnea events, RV pressures may decrease due to ineffective inspiratory efforts against a closed airway, causing negative intrathoracic pressure. During a recovery or arousal from an apnea event, the pressure may increase briefly. This situation is shown graphically in FIG. 2 in the plot labeled PRESSURE (mmHg). The top line, $P_H$ 26, is a plot of an upper percentile value (e.g., the $94^{th}$ percentile) representative of the upper range of a hemodynamic pressure parameter (e.g., RVDP), measured and plotted at periodic storage intervals (e.g., six minute intervals). The bottom line, $P_L$ 30, is a plot of a lower percentile value (e.g., the $6^{th}$ percentile) representative of the lower range of the same hemodynamic pressure parameter over the same storage intervals as plotted for $P_H$. The line plotted between $P_H$ 26 and $P_L$ 30 is, in this example, the median value of the hemodynamic pressure parameter plotted over the same storage intervals, and is designated $P_M$ 40. It should be noted that the choice of the $6^{th}$ and $94^{th}$ percentiles as the lower and upper percentile values is meant to be by way of example only; other percentile values could have been chosen to reflect the distribution of data without departing from the scope of the invention. Similarly, the choice of RVDP as the hemodynamic pressure parameter, as well as the choice of six minutes as the storage interval, and the use of the median (rather than the mean or the mode, for example) for the $P_M$ parameter, are all considered exemplary, since other choices for these parameters would become apparent to one of ordinary skill in the art with the benefit of these teachings.

Figure 2:
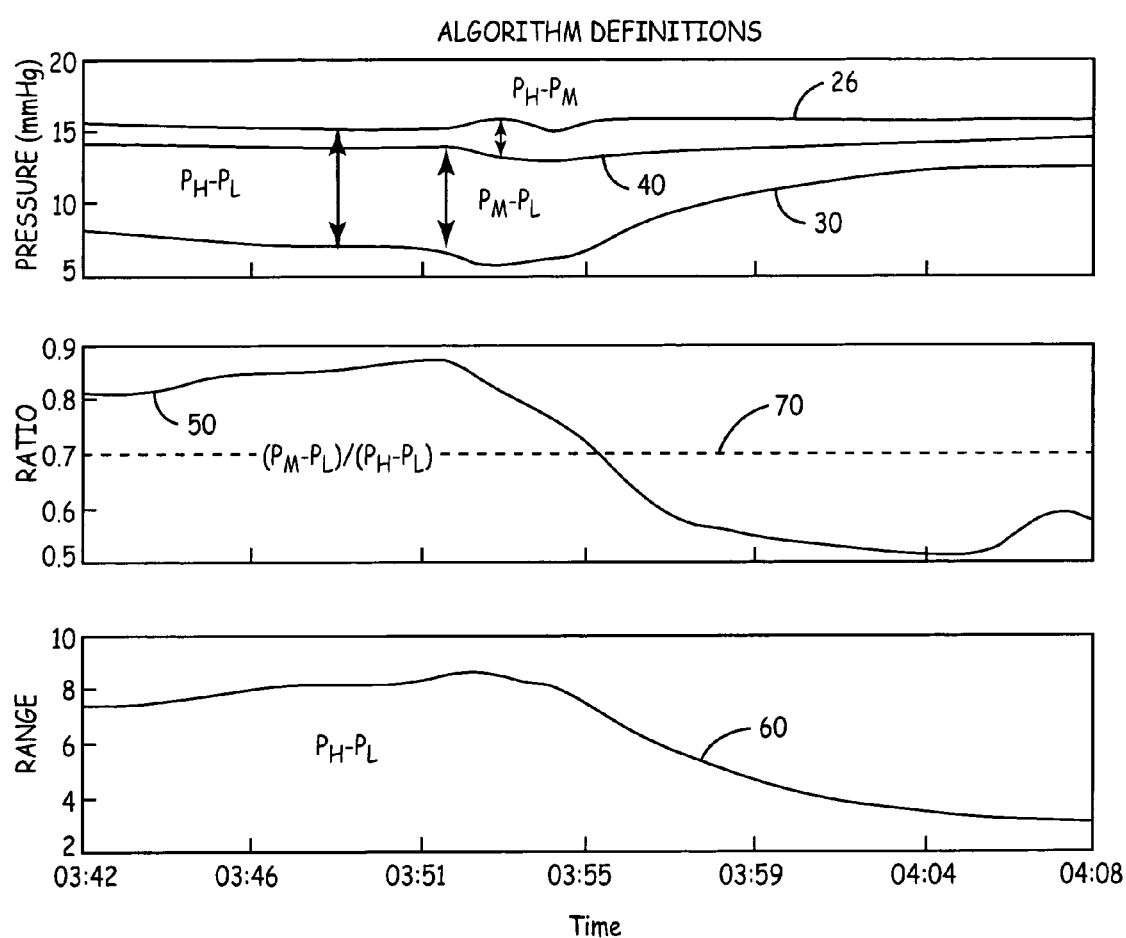
FIG. 2 is a series of plots of a hemodynamic pressure parameter signal and various other parameters derived therefrom in accordance with an embodiment of the invention.

With continued reference to FIG. 2, the recurrence of apnea-recovery cycles over a period of time may tend to cause the lower percentile value of the hemodynamic pressure parameter, $P_L$, to decrease along with a corresponding increase in the value of the parameter range, $P_H$-$P_L$. The median value, $P_M$, tends to remain relatively unaffected.

According to an embodiment of the invention, an SDB episode may be detected by calculating a ratio of the lower portion of the parameter distribution to the full range, $P_{Range}$ 60, of the parameter distribution, then comparing the ratio to a predetermined threshold criterion. This ratio may also be described as the skewness of the sample distribution of the hemodynamic pressure parameter. If the ratio, $P_{Ratio}$ 50, is greater than the threshold, for example, then SDB may be suspected. One way of performing this ratio calculation is by taking the difference between the $P_M$ 40 and $P_L$ 30 values and dividing by the difference between the $P_H$ 26 and $P_L$ 30 values, as follows:

$$P_{Ratio}=(P_M-P_L)/(P_{Range})=(P_M-P_L)/(P_H-P_L),$$

where $$P_{Range}=(P_H-P_L).$$

In FIG. 2, the $P_{Ratio}$ 50 is plotted as a function of time in the second plot, labeled RATIO. As one possibility, a ratio threshold criterion 70 could be set to a value of 0.7, for example, and used with the particular data shown in FIG. 2 to differentiate between SDB and non-SDB periods. Other values for the ratio threshold criterion 70 may be derived from historical data or past experience, and may be a variable, user-selectable, programmable setting.

Figure 3:
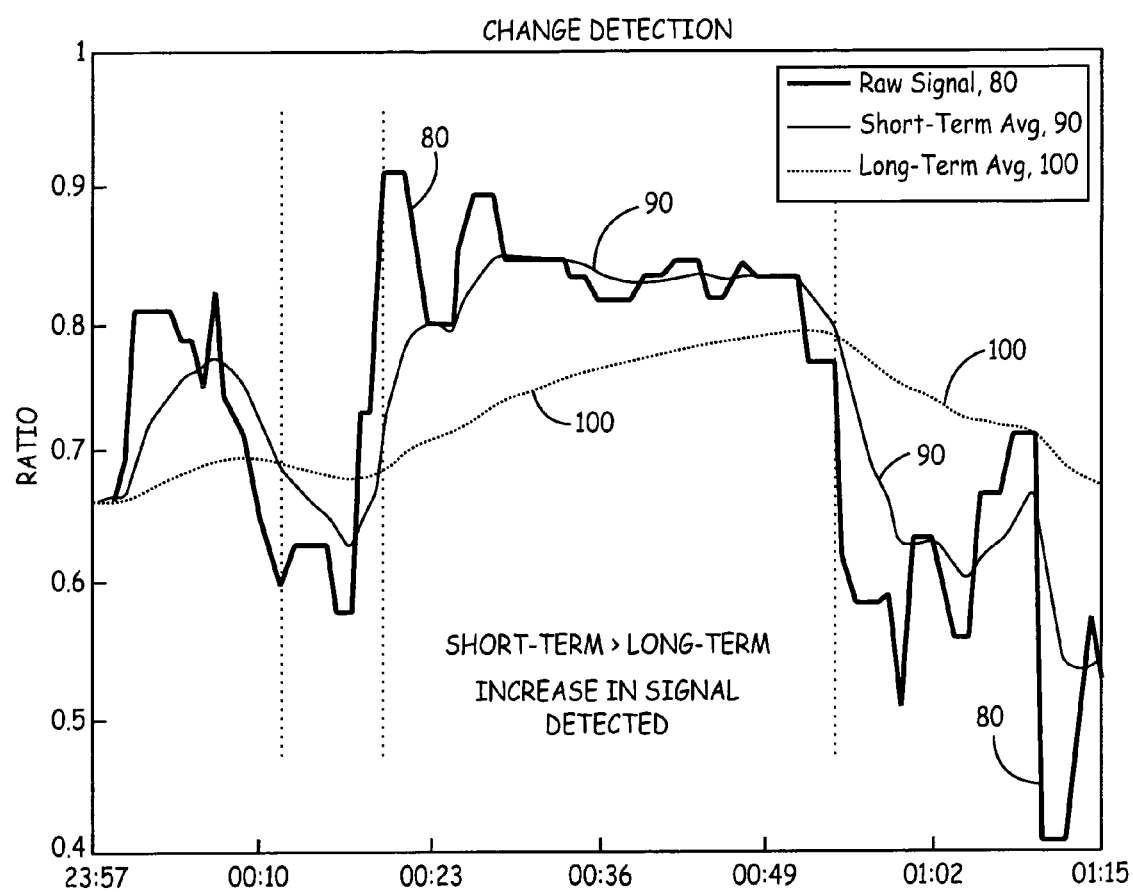
FIG. 3 is a plot showing the use of short-term and long-term averages to detect increases in a hemodynamic pressure parameter signal in accordance with certain embodiments of the invention.

In a further embodiment of the invention, an SDB episode may be detected by evaluating trends in both the $P_{Ratio}$ 50 and in the $P_{Range}$ 60, $P_H$-$P_L$. In one embodiment of the invention, an SDB event may be detected when the $P_{Ratio}$, $(P_M-P_L)/(P_H-P_L)$, and the $P_{Range}$, $(50\ P_H-P_L)$, are both increasing. Various methods of determining whether and/or when the $P_{Ratio}$ 50 and/or $P_{Range}$ 60 are increasing (or decreasing) may be employed. In one embodiment, a fast-moving average (i.e., an average based on relatively recent data, also referred to as a short-term rolling average) may be compared to a slow-moving average (i.e., an average that incorporates older data, also referred to as a long-term rolling average) to determine whether the $P_{Ratio}$ 50 or $P_{Range}$ 60 are increasing or decreasing. For example, if a fast-moving average of the $P_{Ratio}$ 50 is greater than the corresponding slow-moving average, then the $P_{Ratio}$ 50 may be deemed to be increasing. An increase in the $P_{Range}$ 60 could be similarly determined. According to an embodiment of the invention, if both the $P_{Ratio}$ and $P_{Range}$ are deemed to be increasing at the same time, then SDB is suspected. The use of short-term and long-term rolling averages (e.g., 5-point and 30-point rolling averages, respectively) of a raw signal to detect increases and decreases in the raw signal is illustrated in FIG. 3. Both types of rolling averages tend to smooth the raw signal 80 to some extent. However, the short-term average 90 tends to track the raw signal 80 more closely, while the long-term average 100 tends to respond more slowly to changes in the raw signal 80.

Other methods for determining when a signal is increasing may be equivalently employed. An alternate method of determining when the $P_{Ratio}$ 50 and/or $P_{Range}$ 60 are increasing may, for example, include calculating the derivatives of the signals and evaluating whether they are positive. The methods described are by way of illustration, and not limitation, as other methods of determining whether a signal is increasing will be apparent to those having ordinary skill in the art.

In certain other embodiments of the invention, an activity level signal may also be measured and recorded by an IHM and used in conjunction with other indications of sleep apnea, as a way to confirm the presence of an SDB episode. For example, an activity signal may be acquired by an activity sensor to provide a measure of the activity level of the patient. In a true SDB episode, the patient should be asleep, which should be associated with a low activity level. If the presence of SDB is suspected based upon the aforementioned ratio and/or range calculations discussed above, the activity level (possibly measured in terms of "activity counts") measured during the same period of time as the ratio and range calculations may be used to confirm the presence of SDB. This confirmation step may involve comparing the measured activity level to a predetermined activity threshold value, and evaluating whether it is below the threshold. A "low" activity level (i.e., a sensed activity level below the predetermined activity threshold) could be used to confirm that an SDB episode detected by the above-described ratio and range calculations using hemodynamic pressure parameters actually occurred during periods of sleep. An activity sensor may therefore be used as a cross-check to verify that a detected SDB or sleep apnea episode occurs when the patient is at a resting level of activity indicative of a sleep condition.

To produce the activity level signal, an activity sensor may be incorporated as a piezoelectric element sensitive to body movements such that a signal from the activity sensor is correlated to the level of a patient's activity. An accelerometer may also be used to detect when a patient moves or is otherwise physically active. The use of activity sensors is known in the art of rate-responsive pacemakers, and may be implemented as generally disclosed in commonly assigned U.S. Pat. No. 5,052,388 to Sivula, et al., incorporated herein by reference in its entirety. Alternative implementations of activity sensors for use in rate-responsive pacemakers are generally disclosed in U.S. Pat. No. 4,428,378 to Anderson; U.S. Pat. No. 4,896,068 to Nilsson; U.S. Pat. No. 4,869,251 and to Lekholm et al., all of which are incorporated herein by reference in their respective entireties.

Figure 4:
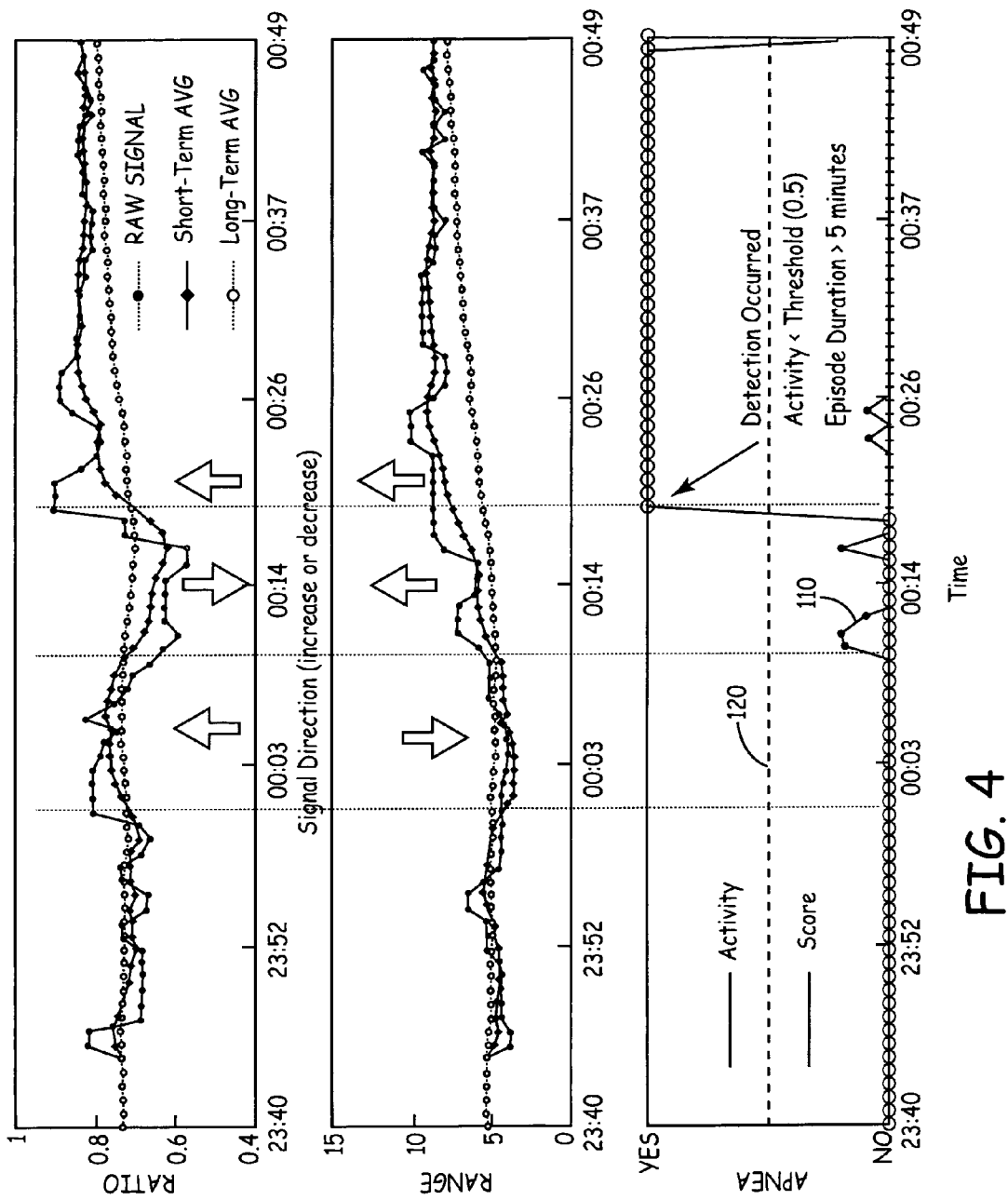
FIG. 4 is a plot showing the use of an activity level signal to confirm the presence of an SDB episode in accordance with an embodiment of the invention.

FIG. 4 illustrates the use of an activity level signal 110 to confirm the presence of an SDB episode detected by identifying an increase in both the $P_{Ratio}$ 50 and $P_{Range}$ 60. In the embodiment of the invention illustrated in FIG. 4, an activity level threshold 120 is set to 0.5 activity counts such that an activity level signal 110 below 0.5 activity counts confirms a sleeping condition.

Additionally, other methods for detecting when a patient is likely to be asleep are known for use in cardiac rhythm management devices, and may provide a basis for confirming the presence of an SDB episode. Such methods may be based on one or more sensor inputs in conjunction with a real-time clock. Sensor signals that may be used for detecting a sleeping state may include an activity sensor, a respiration sensor, a posture sensor, a blood temperature sensor, etc. An implantable multi-axis position and activity sensor is disclosed in U.S. Pat. No. 5,233,984, issued to Thompson, incorporated herein by reference in its entirety. A device capable of determining when a patient is likely to be asleep is disclosed in U.S. Pat. No. 5,630,834, issued to Bardy and U.S. Pat. No. 5,814,087 issued to Renirie, both incorporated herein by reference in its entirety. The devices and methods for determining when a patient is likely to be asleep may be used to confirm the presence of SDB episodes detected by the use of hemodynamic pressure parameters alone.

A further embodiment of the invention may include a confirmation step that may further increase the specificity of detection of SDB episodes by requiring that the detection of SDB persist for a specified duration. For example, in an embodiment of the invention in which the hemodynamic pressure parameter ratio and range calculations, as well as the activity level, are all required to meet specified criteria to detect SDB (e.g., $P_{Ratio}$ and $P_{Range}$ both increasing and activity level less than an activity level threshold), this confirmation step could further require that detection be maintained or sustained for at least X out of the last Y consecutive samples, according to one embodiment of the invention. One particular version of this confirmation step may, for example, include satisfying the detection criteria for a certain number, X, of consecutive samples, or for a certain sustained period of time, T. In FIG. 4, for example, a sustained period of 5 minutes is required in order to detect an SDB episode.

Figure 5:
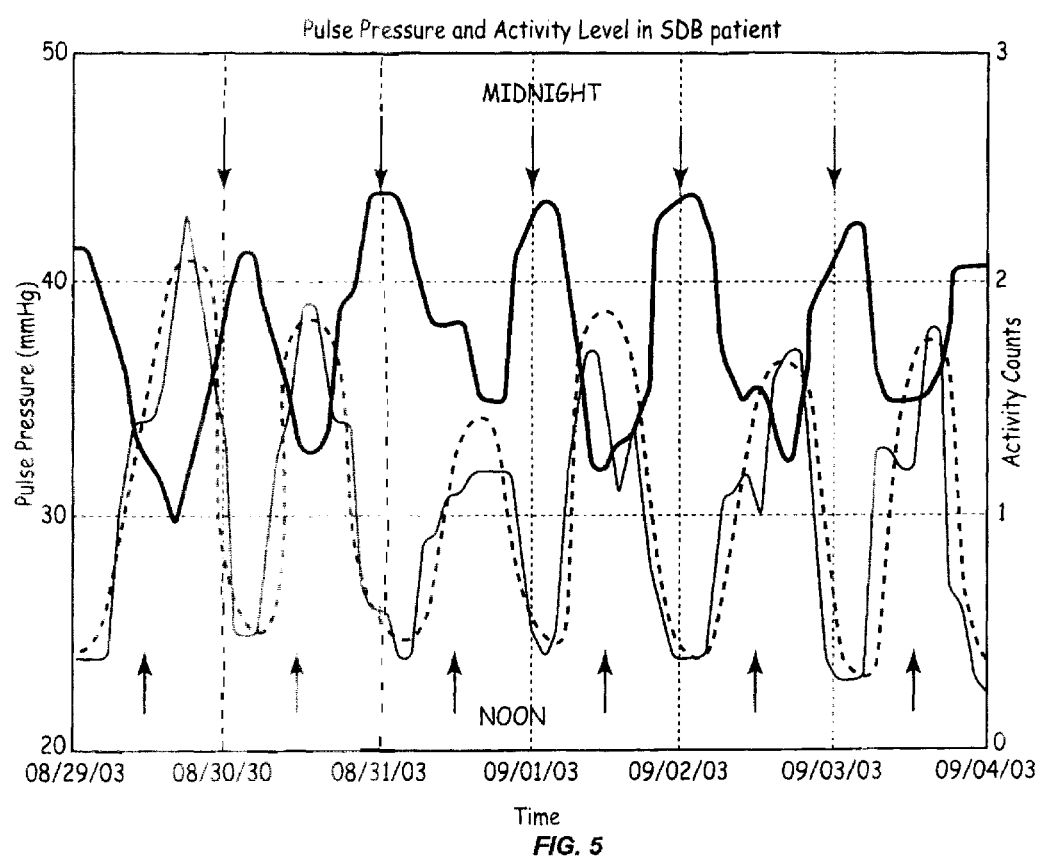
FIG. 5 is a plot of a hemodynamic pressure parameter and an activity level signal over a period of several days for a patient with an SDB condition.

FIG. 5 illustrates patterns of recorded data for a patient presenting with SDB. FIG. 5 includes plots of a hemodynamic pressure parameter and an activity level signal over a period of several days superimposed on the same graph. The hemodynamic pressure parameter may be right ventricular systolic pressure (RVSP), right ventricular diastolic pressure (RVDP), or any other hemodynamic parameter that may be measured and recorded, including parameters derived from other measured parameters. The activity level (activity counts) typically indicates a daily circadian pattern, showing a pattern of relatively high activity counts during the day when the patient is awake, and relatively low activity counts at night when the patient is expected to be asleep. The hemodynamic pressure parameters for a "normal" patient (i.e., a patient without SDB) tend to generally follow the pattern of activity level, resulting in a degree of correlation between the two signals that causes them to appear "in phase" with each other. This "normal" hemodynamic pressure profile is generally represented by the dashed line in FIG. 5, which roughly tracks the activity level signal and which generally corresponds to a daily circadian pattern. By contrast, patients with SDB tend to present with the paradoxical pattern shown in FIG. 5, where the hemodynamic pressure parameter (indicated by the darkened line) and activity level signals appear to have a "phase difference" between them that, in some cases, may be at or near 180 degrees "out of phase." Additionally, the hemodynamic pressure parameter may exhibit large fluctuations at night during periods of relatively little activity.

A measure of the correlation between the blood pressure parameter and the activity level signal (e.g., a correlation coefficient) can be used to quantify the phase difference between the two signals. The measure of correlation may be used to identify the presence of SDB, for example, if the correlation is less than a predetermined threshold. This measurement may also be used to quantify the severity of SDB.

Figure 6:
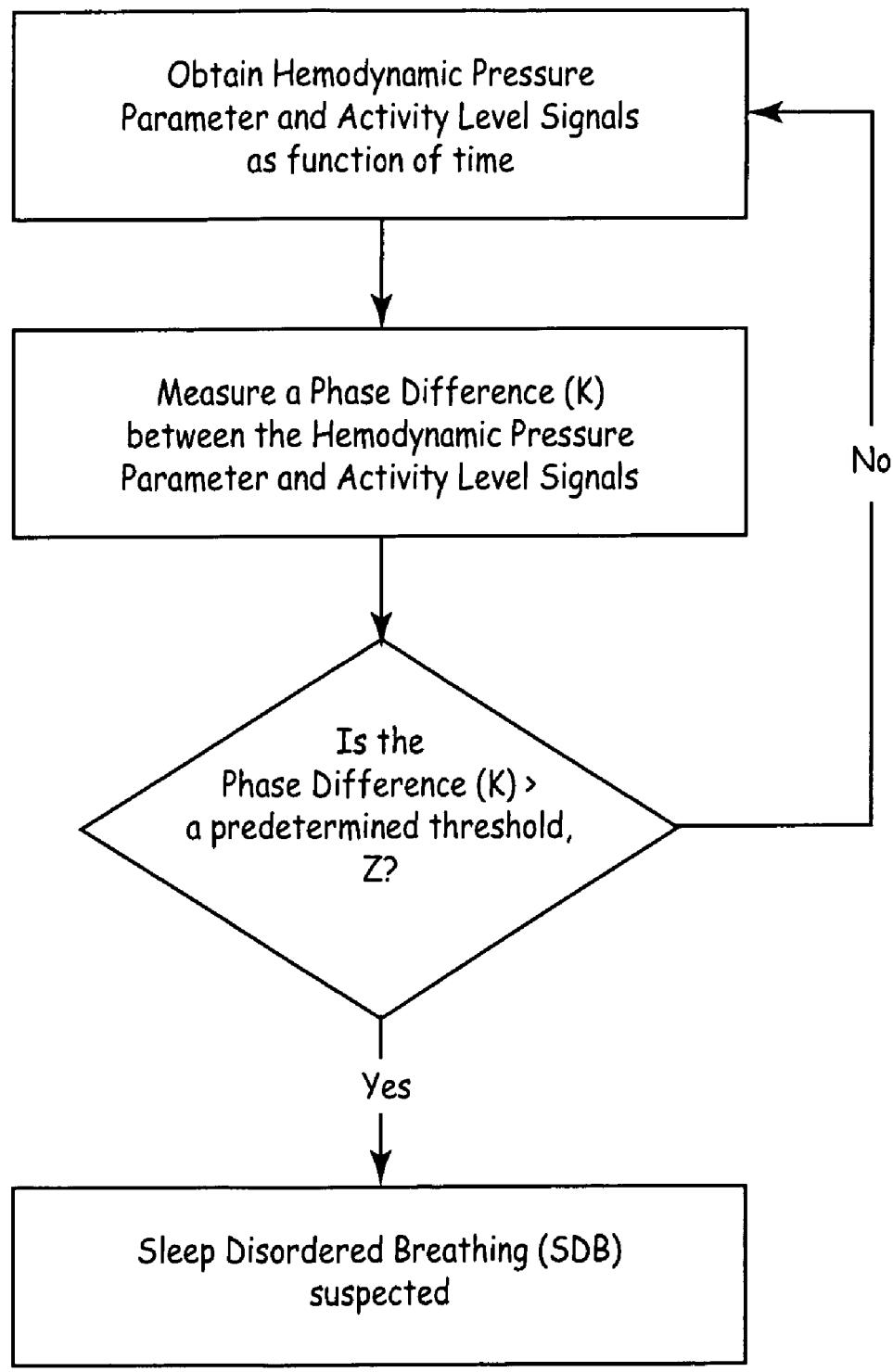
FIG. 6 is a flow chart illustrating a method of screening a patient for the presence of SDB in accordance with an embodiment of the invention.

FIG. 6 is a flow chart that illustrates a method of screening a patient for the presence of SDB based on a measured phase difference between a hemodynamic pressure parameter and an activity level signal. The method illustrated in FIG. 6 includes the following steps:

Step 1: Obtain signals related to a hemodynamic pressure parameter and to an activity level, and record the signals as a function of time. The hemodynamic pressure parameter may be the right ventricular diastolic pressure (RVDP), for example. In certain embodiments of the invention, the median value of the RVDP over a storage interval is recorded as a function of time for comparison to the activity level signal. The activity level signal may also be a median value over each storage interval, or may alternately be a mean value or other similar representative value for each storage interval.

Step 2: Measure the Phase Difference between the hemodynamic pressure parameter and activity level signals. The phase difference may be measured in terms of a "phase angle" difference (i.e., a number of degrees, with a 180 degree difference indicating two signals completely out of phase). Alternately, the phase difference between the two signals may be quantified by using various measures of correlation (e.g., a correlation coefficient). In one embodiment of the invention, a method of quantifying the phase difference between two signals includes calculating and comparing the first derivatives of both signals, and evaluate how frequently the derivatives have the same polarity (e.g., as a percentage). For example, two signals that are out of phase may have first derivatives that are of the same polarity for a relatively small percentage of the time.

Step 3: Determine whether the measured Phase Difference is greater than a predetermined threshold amount, Z. A predetermined threshold, Z, may be selected or chosen from historical data, for example, and may be adjusted according to certain embodiments of the invention to appropriately identify the existence of sleep apnea for a given patient.

Step 4: If the Phase Difference is greater than Z, sleep disordered breathing (SDB) is suspected. If the Phase Difference is less than Z, SDB is not suspected, and monitoring of the hemodynamic pressure parameter and activity level signals may be continued.

A threshold amount of phase difference may be selected to indicate the presence of SDB. For example, if the measured phase difference, K, is greater than a predetermined threshold, Z, then SDB is suspected. If the phase difference is measured in degrees, for example, the threshold, Z, may be chosen such that SDB is indicated by a phase angle difference of 180 degrees plus or minus a certain range. Alternately, the threshold, Z, may be defined in terms of a correlation coefficient (e.g., less than −0.5), or a p-value below a specified level, or the first derivatives of the two signals having the same polarity less than 25% of the time, for example.

Hemodynamic pressure parameters that may be used in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

Figure 7:
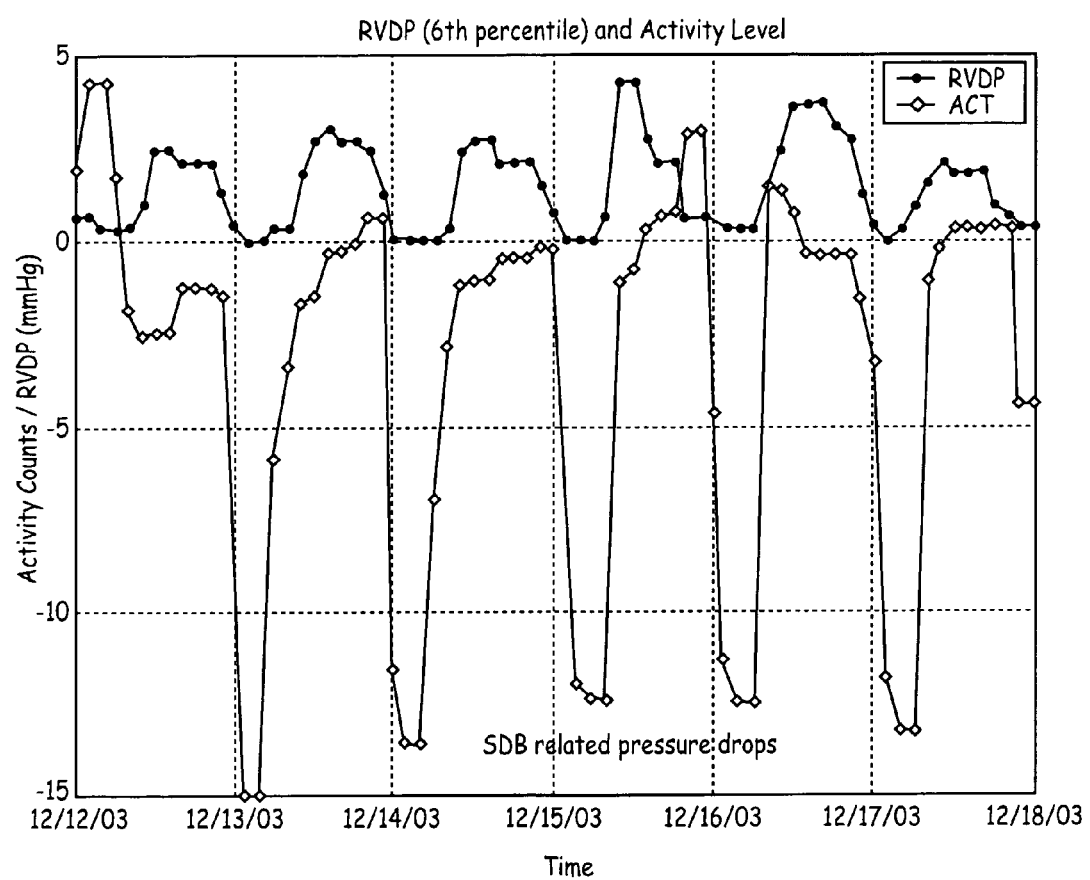
FIG. 7 is a plot of a hemodynamic pressure parameter and an activity level signal.

Another method of screening for the presence of SDB involves detecting the presence of large changes in a hemodynamic parameter during periods of low activity level corresponding to a sleep state. FIG. 7 illustrates an example of a hemodynamic pressure parameter (in this example, the $6^{th}$ percentile RVDP signal) plotted along with an activity level signal over a period spanning about 6 days. The $6^{th}$ percentile RVDP signal in FIG. 7 exhibits a large amount of variability during periods when activity level is nearly zero. According to one embodiment of the invention, an SDB episode may be detected when 1) Activity Level is Low (i.e., activity counts are below a specified level) AND/OR a normal sleep period is occurring (e.g., from about Midnight to about 6:00 a.m.), AND 2) the RVDP lower percentile value drops below a specified level (typically less than about 0 mm Hg).

Figure 8:
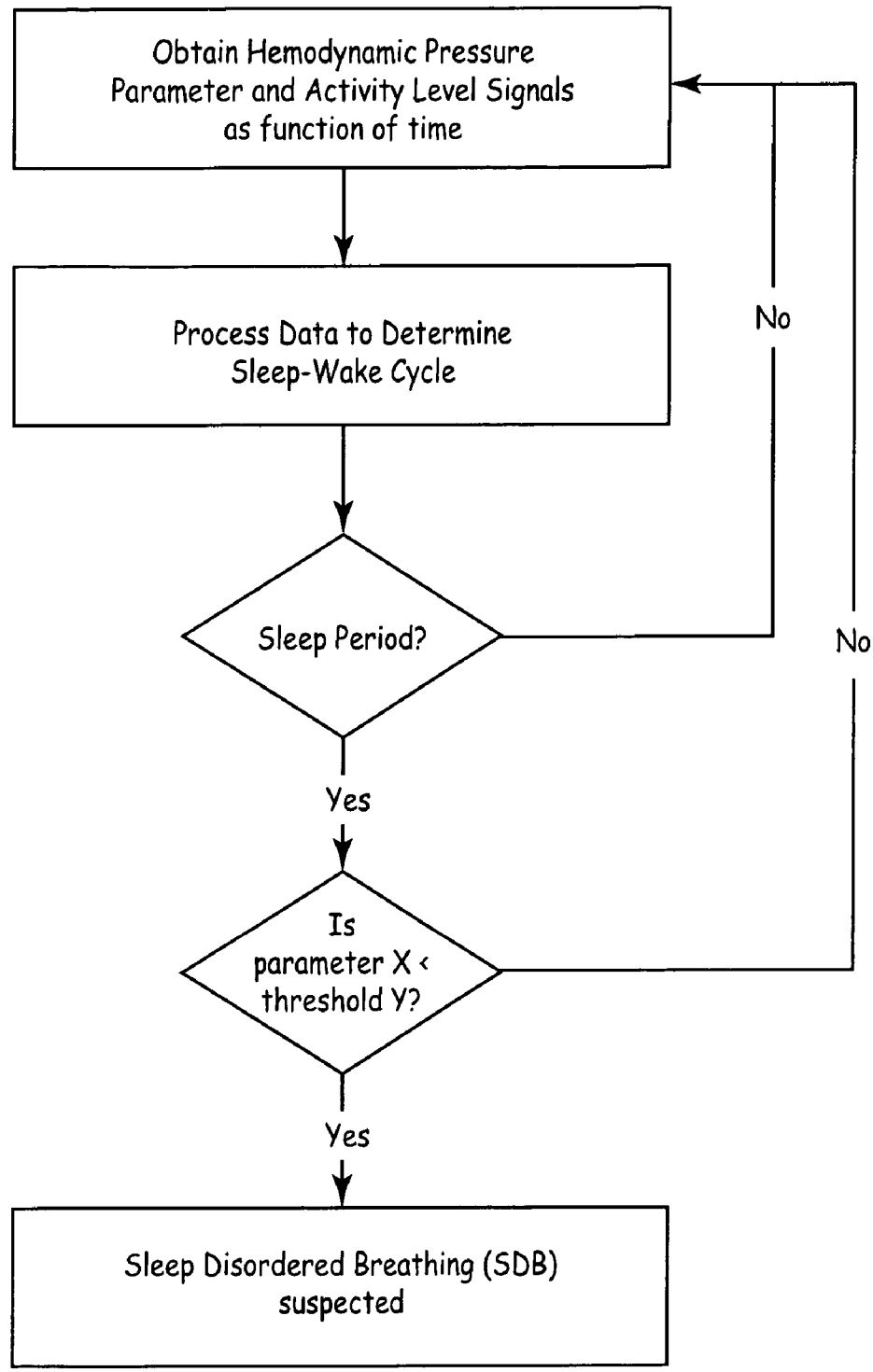
FIG. 8 is a flow chart illustrating a method of screening a patient for the presence of SDB in accordance with an embodiment of the invention.

FIG. 8 is a flow chart that illustrates a method of screening a patient for the presence of SDB based on the above-described decrease in the hemodynamic pressure parameter. The method illustrated in FIG. 8 includes the following steps:

Step 1: Obtain signals related to a hemodynamic parameter (such as blood pressure) and to an activity level, and record the signals as a function of time.

Step 2: Process the activity level signal to identify Sleep portions of a Sleep-Wake cycle. This step may involve further requiring that both a) activity level is low (e.g., activity counts are below a threshold level for a certain period of time), AND b) that the period of time is during normal sleeping hours (e.g., between Midnight and 6:00 a.m.). It should be noted that certain embodiments of the invention could provide for the identification of a sleep period when either of the above conditions are met (e.g., an OR condition). It may further be desirable to allow for a user to select between AND and OR combinations, depending on patient-specific factors, for example.

Step 3: For each identified Sleep portion, compare the hemodynamic parameter to a threshold value. If the threshold is exceeded, SDB is suspected; if not, monitoring continues. The threshold value may, for example, be a value that the hemodynamic pressure parameter must decrease below in order to cause SDB to be suspected. Alternately, the threshold may be a specified amount of decrease in the hemodynamic pressure parameter (i.e., a "delta") that must occur within a certain amount of time in order to suspect an SDB condition.

Evaluating Effectiveness of SDB Therapy.

Figure 9:
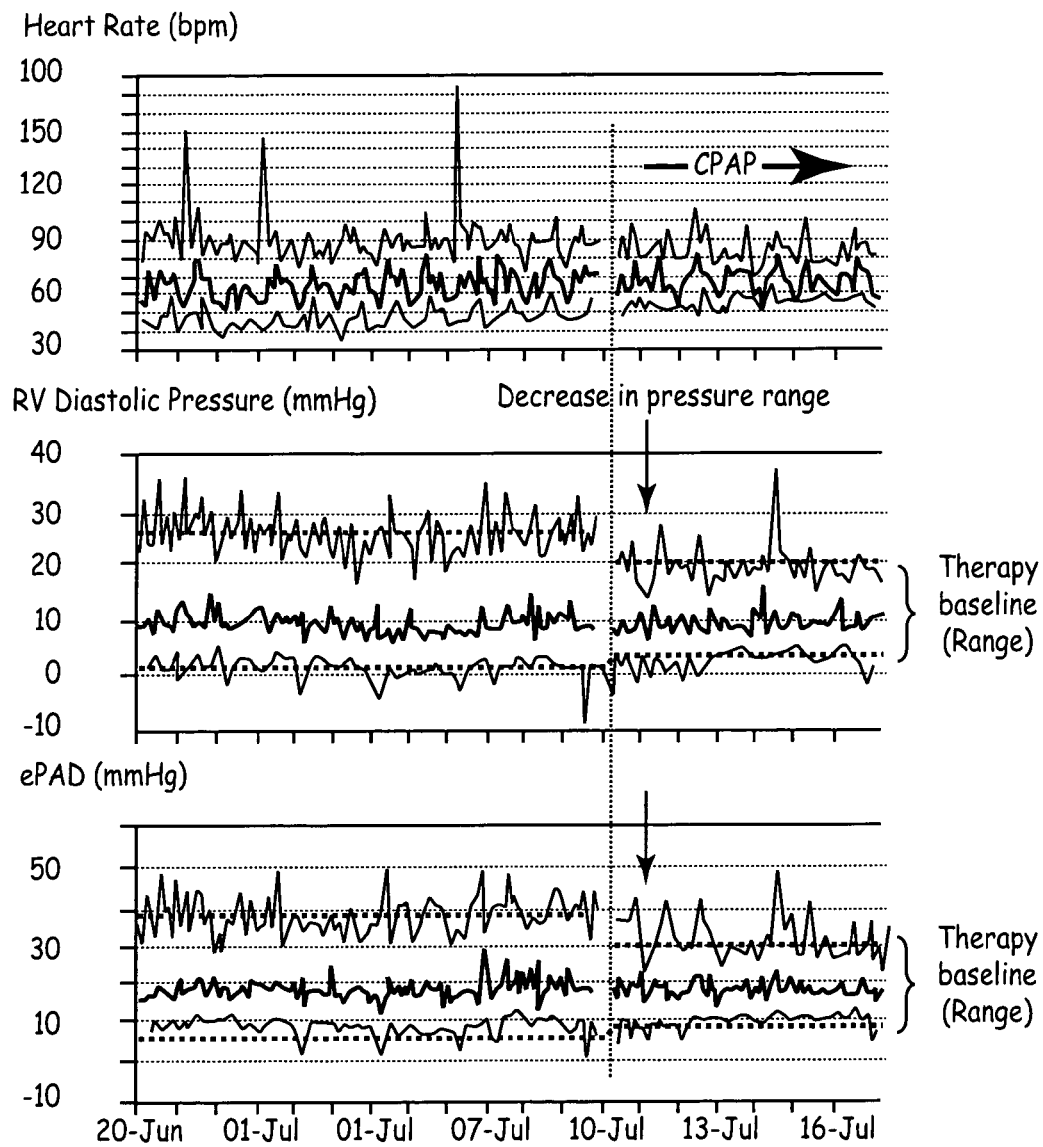
FIG. 9 is a series of plots showing the effect of an SDB therapy on hemodynamic pressure parameters.

In patients who have been diagnosed with SDB, a system such as the Medtronic® Chronicle™ system can also be used to monitor the effectiveness of SDB therapy. For example, continuous positive airway pressure (CPAP) is one form of SDB therapy. CPAP attempts to reduce ventricular pressure variability associated with SDB by alleviating SDB, and by preventing intrathoracic pressure from falling. FIG. 9 illustrates the effect that CPAP therapy may have on pressure parameters of interest. Successful CPAP therapy may, for example, cause a decrease in the measured pressure ranges, as shown in FIG. 9. These new, lower pressure ranges may be used to define a "therapy baseline" (or therapy range) indicative of a desired outcome. If the measured pressures subsequently deviate from an established therapy baseline, a physician or other health care provider may suspect that either the patient is not using the CPAP therapy (a patient compliance issue), or that the CPAP may be ineffective for other reasons, such as an inappropriate pressure setting, or other problems with the CPAP equipment.

Figure 10:
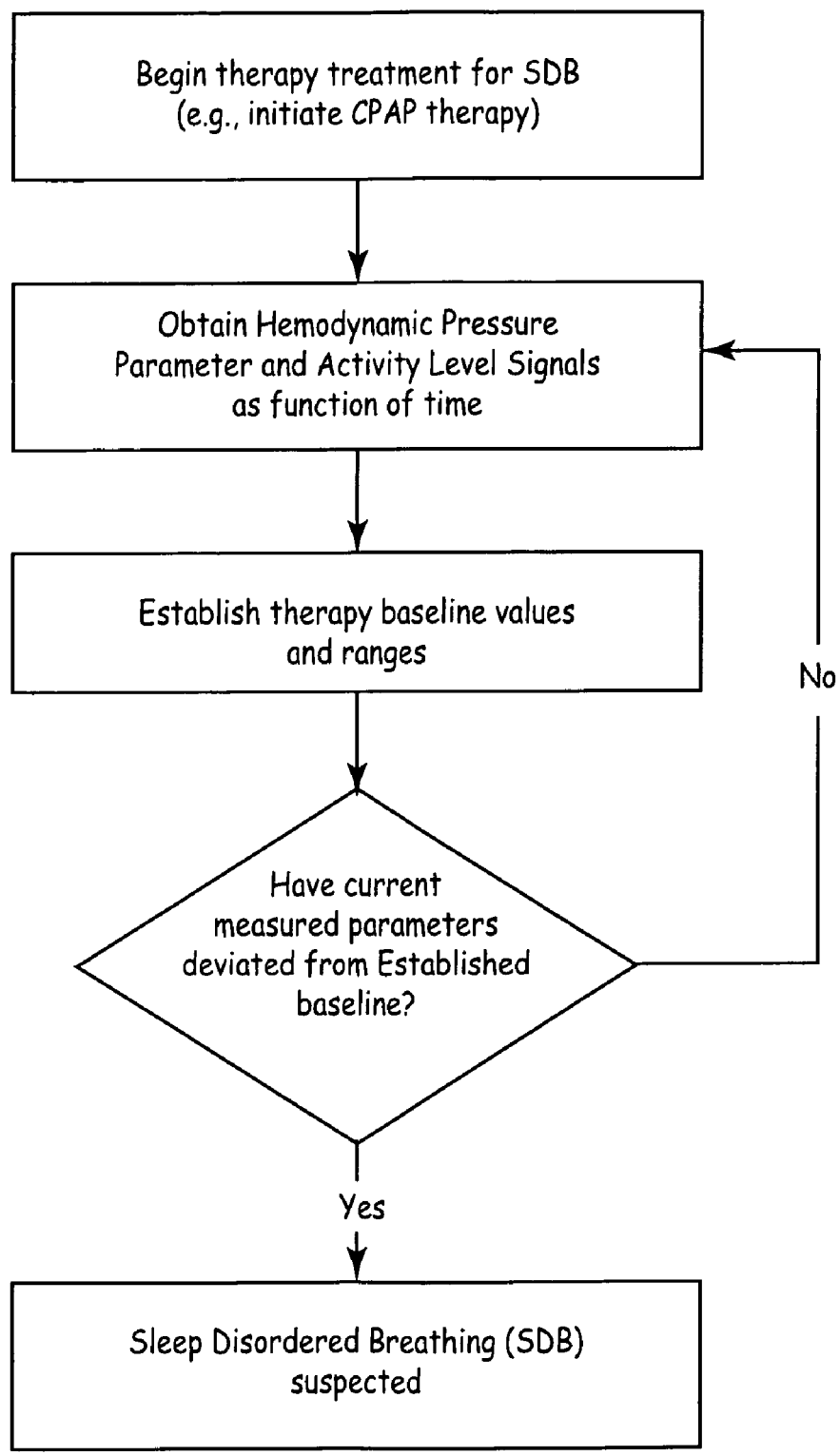
FIG. 10 is a flow chart illustrating a method of evaluating the effectiveness of an SDB therapy in accordance with an embodiment of the invention.

FIG. 10 is a flow chart that illustrates a method of evaluating the effectiveness of an SDB therapy, such as CPAP, on a given patient. The method illustrated in FIG. 10 includes the following steps:

Step 1: Begin treatment for SDB, using a therapy such as CPAP.

Step 2: Obtain signals related to a hemodynamic parameter (such as blood pressure) and to an activity level, and record the signals as a function of time.

Step 3: Establish a therapy baseline for the hemodynamic parameter by observing and recording the hemodynamic parameter during successful application of an SDB therapy, and selecting values representative of acceptable limits for successful SDB therapy.

Step 4: Monitor for a deviation from the established therapy baseline. This step may involve various "change detection" techniques. Change detection may be accomplished by using a comparison of short- and/or long-term averages, as discussed above, or by using a cumulative sum (CUSUM) type of change detector, for example.

Thus, embodiments of a METHOD FOR DETECTING AND MONITORING SLEEP DISORDERED BREATHING USING AN IMPLANTABLE MEDICAL DEVICE are disclosed. One skilled in the art will appreciate that the invention can be practiced with embodiments other than those disclosed. The disclosed embodiments are presented for purposes of illustration and not limitation, and the invention is limited only by the claims that follow.

The invention claimed is:

1. A method of identifying sleep disordered breathing (SDB) episodes in a patient, the method comprising: measuring a hemodynamic pressure of the patient; periodically deriving statistical information about the measured hemodynamic pressure at storage intervals, the statistical information including a high value, a middle value, and a low value representative of the distribution of the hemodynamic pressure over each storage interval; determining a ratio of a lower range to a full range of the hemodynamic pressure, the lower range being equal to a difference between the middle value and the low value, and the full range being equal to the difference between the high value and the low value; and determining whether the patient has experienced an SDB episode based upon the ratio.

2. The method of claim 1, wherein the hemodynamic pressure is right ventricular diastolic pressure.

3. The method of claim 1, wherein the high, middle and low values correspond to predetermined percentile values of the hemodynamic pressure derived over each storage interval.

4. The method of claim 3, wherein the predetermined percentile values of the hemodynamic pressure are the $94^{th}$, $50^{th}$, and $6^{th}$ percentile value over each storage interval.

5. The method of claim 1 wherein the middle value is selected from the group consisting of a median, mean, and mode of the hemodynamic pressure derived over each storage interval.

6. The method of claim 1 wherein determining whether the patient has experienced SDB episodes comprises: comparing the ratio to a predetermined ratio threshold and identifying when the ratio exceeds the predetermined ratio threshold.

7. The method of claim 6 wherein the predetermined ratio threshold is greater than 0.5.

8. The method of claim 6 wherein determining whether the patient has experienced SDB episodes further comprises: monitoring an activity level of the patient and identifying when the activity level exceeds a predetermined activity threshold.

9. The method of claim 8 wherein the activity level of the patient is obtained using one of a piezoelectric sensor and an accelerometer.

10. The method of claim 6 wherein the step of using the ratio to determine whether the patient has SDB episodes further comprises:
    determining whether the ratio exceeds the predetermined ratio threshold for a specified duration.

11. The method of claim 10 wherein the specified duration comprises an interval of time.

12. The method of claim 10 wherein the specified duration comprises at least X out of Y storage intervals.

13. The method of claim 1 wherein determining whether the patient has SDB episodes comprises: identifying when both the ratio and the full range of the hemodynamic pressure are increasing.

14. The method of claim 13 wherein an increase in the ratio and full range of the hemodynamic pressure is determined by comparing a short-term average of the hemodynamic pressure to a long-term average of the hemodynamic pressure.

15. The method of claim 13 wherein an increase in the ratio and full range of the hemodynamic pressure is determined by computing a derivative of the ratio and full range.

* * * * *